504-165 SR
2/16/86 OR RE 32,306

United States Patent [19]
Waters

[11] E Patent Number: Re. 32,306
[45] Reissued Date of Patent: Dec. 16, 1986

[54] INTUBATING DEVICE

[75] Inventor: William E. Waters, Malvern, Pa.

[73] Assignee: Biosearch Medical Products, Inc., Somerville, N.J.

[21] Appl. No.: 742,286

[22] Filed: Jun. 7, 1985

Related U.S. Patent Documents

Reissue of:
[64] Patent No.: 4,388,076
Issued: Jun. 14, 1983
Appl. No.: 233,482
Filed: Feb. 11, 1981

[51] Int. Cl.[4] ..... A61M 25/00
[52] U.S. Cl. ..... 604/165; 604/166
[58] Field of Search ..... 128/207.14, 207.15, 128/200.26, 4, 205.13, 136; 604/54, 77, 95, 170, 164, 165, 280, 283

[56] References Cited

U.S. PATENT DOCUMENTS

| | | | |
|---|---|---|---|
| 2,688,329 | 9/1954 | Wallace | 604/95 |
| 3,070,089 | 12/1962 | Dick | 604/77 |
| 3,128,769 | 4/1964 | Scislowicz | 604/170 |
| 3,395,711 | 8/1968 | Plzak, Jr. | 128/200.26 |
| 3,416,531 | 12/1968 | Edwards | 604/95 |
| 3,503,385 | 3/1970 | Stevens | 604/95 |
| 3,896,815 | 7/1975 | Fettel et al. | 128/348.1 |
| 3,957,055 | 5/1976 | Linder et al. | 128/200.26 |
| 3,964,488 | 6/1976 | Ring et al. | 128/207.14 |
| 4,033,331 | 7/1977 | Guss et al. | 604/95 |
| 4,249,535 | 2/1981 | Hargest, III | 604/54 |

FOREIGN PATENT DOCUMENTS

| | | | |
|---|---|---|---|
| 327698 | 6/1903 | France | 128/349 R |

*Primary Examiner*—Henry J. Recla
*Attorney, Agent, or Firm*—Hoffmann, Dilworth, Barrese & Baron

[57] ABSTRACT

An intubating device has a flexible tube with an open proximal end and a discharge opening adjacent its distal end. A hollow stylet connector plug is removably secured to the proximal end of the tube. A stylet is secured to the plug and extends through the interior of the tube to a point adjacent the distal end of the tube. The stylet has an outer diameter smaller than the inner diameter of the tube and smaller than the inner diameter of the plug to permit the passage of fluid between the stylet and the tube and between the stylet and the plug. A hollow connector fitting is integral with the plug and has a passage communicating with the interior of the plug. A stop accurately locates the stylet with respect to the tube preferably extending the tube.

11 Claims, 5 Drawing Figures

INTUBATING DEVICE

Matter enclosed in heavy brackets [ ] appears in the original patent but forms no part of this reissue specification; matter printed in italics indicates the additions made by reissue.

TECHNICAL FIELD

This invention is in the field of devices used for medical treatment.

BACKGROUND OF THE PRIOR ART

It is well known in the prior art to use stylets within tubes to be inserted into a body in order to stiffen the tube to facilitate insertion as seen, for example, in U.S. Pat. Nos. 873,275, 2,188,631, 2,164,926, 3,397,699, 3,467,101, 3,672,372, 3,726,283, 3,924,632, 3,957,005, 4,073,287, 4,073,297, 4,111,190, 4,148,319, 4,155,364, and 4,160,446. Nasogastric and Nasojejunal tubes are widely used for hyperalimentation. It is frequently necessary to employ stylets with these tubes in order to introduce them into the correct position in the patient. Existing devices require the physician to either confirm the location of the tips of such tubes by X-ray, which in some cases is an unnecessary expense and an added risk to the patient, or to remove the stylet and confirm the tube position by using other procedures. These procedures include auscultation using air, injection of small quantities of water, and aspiration of gastric contents for identification. With all of these procedures the stylet is removed conventionally. If the tube is found to be improperly positioned, the stylet must be reintroduced into the tube in the patient which involves the risk that the stylet will pass through the tube and puncture soft gastrointestinal or respiratory tissues. This risk is unacceptable and avoided by removing the tube and then reintroducing it after the stylet has been inserted into the tube. This involves discomfort for the patient and a loss of time. The problem is greatly aggravated when it takes several repetitions of the procedure before the tube is found to be in the proper position.

In accordance with the invention, the above problem is solved by having a combined tube and stylet which permits the carrying out of the above discussed procedures without the removal of the stylet.

BRIEF SUMMARY OF THE INVENTION

An intubating device has a flexible tube with an open proximal end and a discharge opening adjacent its distal end. A hollow stylet connector plug is removably secured to the proximal end of the tube. A stylet is secured to the plug and extends through the interior of the tube to a point adjacent the distal end of the tube. The stylet has an outer diameter smaller than the inner diameter of the tube and smaller than the inner diameter of the plug to permit the passage of fluid between the stylet and the tube and between the stylet and the plug. A hollow connector fitting is integral with the plug and has a passage communicating with the interior of the plug. A stop accurately locates the stylet with respect to the tube, preferably extending the tube.

DETAILED DESCRIPTION

Figure 4:
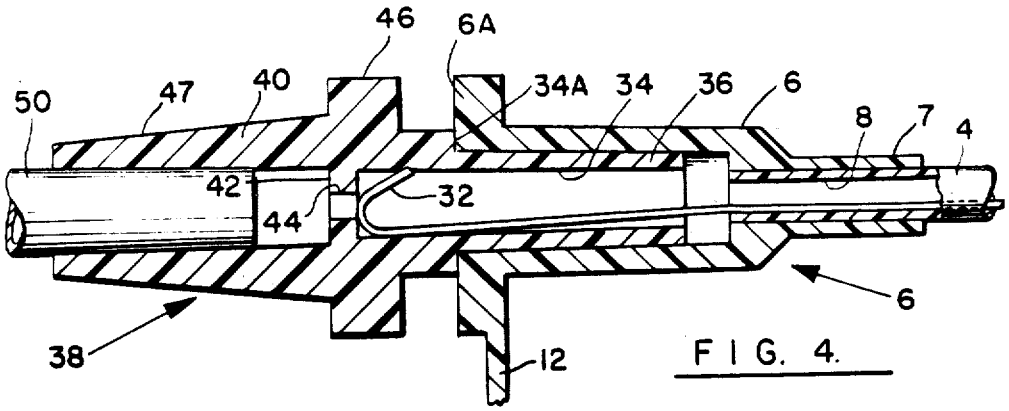
FIG. 4 is an enlarged vertical section of the integral plug and connector fitting of the intubating device of FIG. 3.
Figure 3:
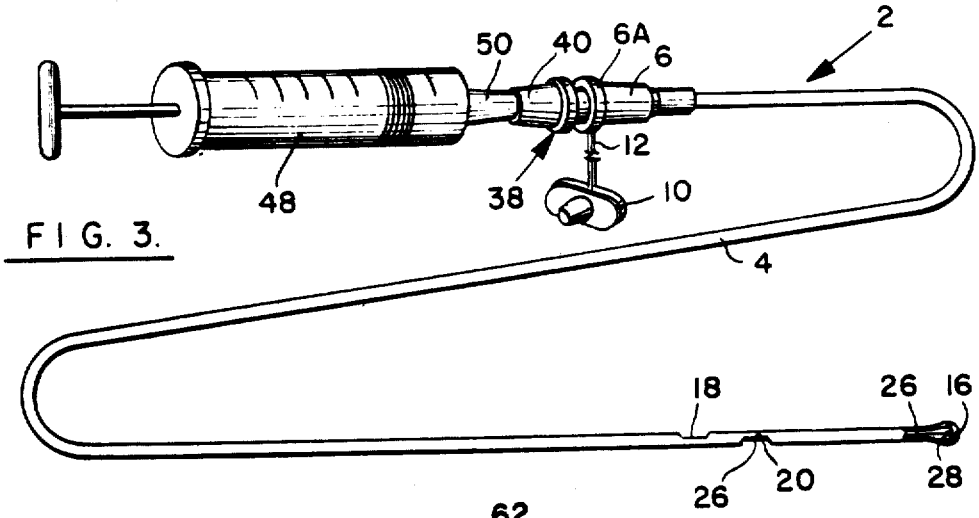
FIG. 3 is a plan view of an intubating device in accordance with the invention, partially broken away.

Referring to FIG. 3, an intubating device 2 useful, for example, for enteric feeding has a flexible tube 4 of any material conventionally used for such tubes such as polyurethane, polyethylene or polyvinylchloride. A female luer connector 6 has a reduced portion 7 (FIG. 4) in which is secured the proximal end 8 of tube 4. Connector 6 has a closure plug 10 secured thereto by an integral flexible strap 12. The distal end 16 of tube 4 is closed. Adjacent distal end 16 are openings 18 and 20 for the passage of fluid into or out of tube 4.

Figure 1:
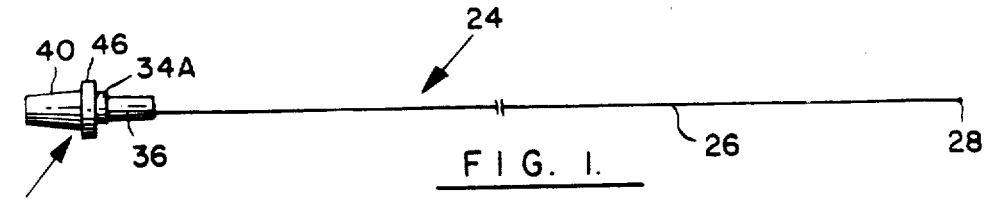
FIG. 1 is a plan view of a stylet in accordance with the invention, partially broken away.
Figure 2:
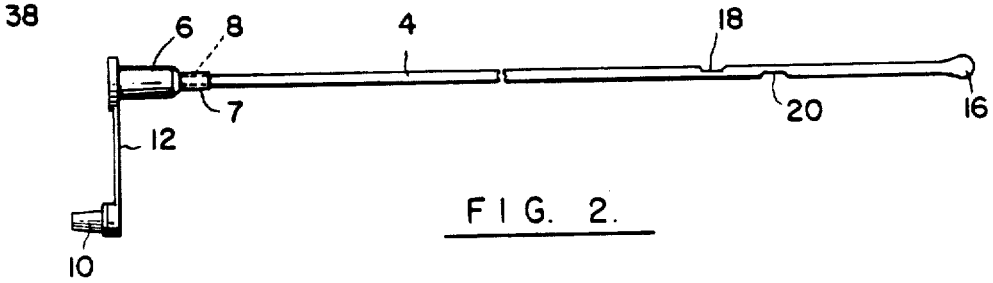
FIG. 2 is a plan view of an intubating tube.

A stylet 24 has a wire body 26 (FIG. 1) the distal end 28 of which is slightly enlarged in the form of a ball and is located adjacent the distal end 16 of tube 4 (FIG. 3). The proximal end 32 of wire 26 is formed into a hook (FIG. 4) which engages the inside wall 34 of a hollow plug 36 of connector 38. Plug 36 is secured by a pressed fit inside luer connector 6. A stop shoulder 34A on plug 36 is engaged by the flanged end 6A of luer connector 6 to provide for precise positioning of the stylet with respect to the tube 4 with stylet 24 extending tube 4 slightly to insure that the end 28 cannot pull back and pass through one of openings 18 or 20. The wire is preferably steel such as stainless steel. Connector 38 is preferably made of a synthetic resin such as polyethylene, polypropylene or polyvinylchloride which the hook end 32 can indent slightly.

Integral with plug 36 in connector 38 is a female luer connector 40. A wall 42 separates the interior of connector 40 and plug 36, but this wall has an opening 44 which is big enough for the passage of fluid but too small to permit passage of the proximal hook end 32 of wire body 26. A raised ring portion 46 of connector 40 facilitates the minipulation of the connector 40 and plug 36. The exterior 47 of connector 40 is shaped to cooperate with a standard syringe locking sleeve (not shown) when one is used.

As seen in FIG. 3, a syringe 48 may conveniently have its nozzle 50 received inside connector 40 for forcing auscultation air through tube 4 for the auscultation procedure or for the aspiration of gastric contents from the patient for tube placement confirmation. After the tube has been satisfactorily positioned, syringe 48 is removed and stylet 24 is removed from tube 4 which may then be connected in a conventional manner for example, to an enteric feeding bag (not shown). In this manner the tube is properly positioned without the necessity for its removal or reinsertion since the stylet is retained in the tube until positioning is completed. Further the device is simple in structure and hence of relatively low cost and easy to handle.

Figure 5:
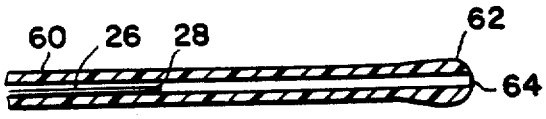
FIG. 5 is an enlarged vertical cross section, partially broken away, of an alternative intubating tube.

In lieu of the openings 18 and 20 the intubating tube may have an open end. Referring to FIG. 5, an intubating tube 60 is identical to tube 4 with the exception that openings 18 and 20 of tube 4 are eliminated, the tube is provided with an enlarged end 62 having an opening 64 and the tube is lengthened sufficiently so that wire 26 cannot protrude through opening 64 beyond tube 60. Typically the opening 64 will be about 2.5 cm beyond the distal end of wire 26 before the tube is inserted into a patient.

The above described embodiments are illustrative and are not intended to be limiting.

I claim:

1. An Enteric feeding device comprising:

[a flexible tube] *a tube having unrestricted flexibility in all directions and* having a self-sustaining diameter, free to be in any position at rest, and having an open proximal end and a discharge opening adjacent its distal end;

a hollow stylet connector plug having an inner diameter and removably secured to the proximal end of the tube;

a stylet [extending into the bore of said plug and] *immovably* secured to said plug *substantially against longitudinal movement therebetween* and extending through the interior of the tube to a point adjacent the distal end of the tube *when the plug is mounted to the proximal end of the tube*;

said stylet having an outer diameter smaller than the inner diameter of the tube and smaller than the inner diameter of the plug for passage of fluid *through said plug and* between the stylet and the tube [and the stylet and the plug]; and a hollow connector fitting integral with said plug and having a passage communicating with the interior of the plug.

2. A device in accordance with claim 1 in which the stylet has a hook at its proximal end engaging the interior of the stylet connector plug.

3. A device in accordance with claim 1 in which the stylet connector plug and the hollow connector fitting are coaxial.

4. A device in accordance with claim 1 in which the distal end of the stylet is in engagement with the distal end of the tube and the stylet extends the distal end of the tube.

5. A device in accordance with claim 4 in which the tip of the distal end of the stylet is enlarged.

6. A device in accordance with claim 1 in which a syringe is connected to the hollow connector fitting.

7. A device in accordance with claim 1 having stop means for accurately positioning the stylet with respect to the tube.

8. A device in accordance with claim 1 in which the discharge opening is in the side of the tube.

9. A device in accordance with claim 1 in which the discharge opening is at the distal end of the tube.

10. An enteric feeding device comprising:

a flexible tube, having an open proximal end, a closed distal end, and a discharge opening adjacent its distal end;

a hollow stylet connector plug having an inner diameter and removably secured to the proximal end of the tube;

a stylet having a hook proximal end engaging the interior of said plug and having an enlarged distal end engaging the interior of the distal end of the tube and extending the tube;

said stylet having an outer diameter smaller than the inner diameter of the tube and smaller than the inner diameter of the plug for passage of fluid between the stylet and the tube and the stylet and the plug;

stop means for accurately positioning the stylet with respect to the tube; and a hollow connector fitting coaxial and integral with said plug and having a passage communicating with the interior of the plug and too small for the passage of the hook end of the stylet.

11. The device of claim 10 in which a syringe is attached to the hollow connector fitting.

* * * * *